(12) United States Patent
Abe et al.

(10) Patent No.: US 7,880,937 B2
(45) Date of Patent: Feb. 1, 2011

(54) ELECTRONIC ENDOSCOPE APPARATUS

(75) Inventors: Kazunori Abe, Saitama (JP); Yoshifumi Donomae, Kawasaki (JP)

(73) Assignees: Fujinon Corporation, Saitama-Shi (JP); FUJIFILM Corporation, Tokyo (JP)

( * ) Notice: Subject to any disclaimer, the term of this patent is extended or adjusted under 35 U.S.C. 154(b) by 1504 days.

(21) Appl. No.: 11/253,632

(22) Filed: Oct. 20, 2005

(65) Prior Publication Data

US 2006/0082645 A1 Apr. 20, 2006

(30) Foreign Application Priority Data

Oct. 20, 2004 (JP) ............................. 2004/305039

(51) Int. Cl.
*H04N 1/04* (2006.01)

(52) U.S. Cl. ................ 358/474; 358/475; 358/483; 358/528; 348/71; 348/E5.038; 348/E9.003; 382/161; 382/278; 600/178; 600/476

(58) Field of Classification Search ............. 358/474, 358/528, 509, 475, 520, 513, 514, 482, 483; 348/71, E5.038, E9.003, 77, 296, 42, 370, 348/E13.001, E5.048; 382/161, 278, 275; 600/101, 109, 476, 171, 178
See application file for complete search history.

(56) References Cited

U.S. PATENT DOCUMENTS

| | | | | |
|---|---|---|---|---|
| 4,974,076 A * | 11/1990 | Nakamura et al. | ............ | 348/71 |
| 5,111,281 A * | 5/1992 | Sekiguchi | .................... | 348/65 |
| 5,124,842 A * | 6/1992 | Honda et al. | ................ | 359/561 |
| 6,254,531 B1 * | 7/2001 | Higuchi et al. | .............. | 600/178 |
| 6,425,858 B1 * | 7/2002 | Minami | ..................... | 600/168 |
| 6,707,485 B1 * | 3/2004 | Higuchi et al. | ................ | 348/69 |
| 6,967,673 B2 * | 11/2005 | Ozawa et al. | ................. | 348/71 |
| 7,419,230 B2 * | 9/2008 | Tatsuta et al. | .................. | 347/5 |
| 7,551,196 B2 * | 6/2009 | Ono et al. | ...................... | 348/65 |
| 2003/0030722 A1 * | 2/2003 | Ozawa et al. | ................. | 348/71 |
| 2005/0093972 A1 * | 5/2005 | Higuchi | ...................... | 348/71 |
| 2007/0046798 A1 * | 3/2007 | Fukuyama et al. | ......... | 348/296 |

FOREIGN PATENT DOCUMENTS

| JP | 6-326917 A | 11/1994 |
|---|---|---|
| JP | 8-338952 A | 12/1996 |
| JP | 11-136693 A | 5/1999 |

* cited by examiner

*Primary Examiner*—Negussie Worku
(74) *Attorney, Agent, or Firm*—Sughrue Mion, PLLC

(57) ABSTRACT

An electronic endoscope apparatus includes an imaging element and a signal processing unit. The imaging element obtains an image of an observation object, and outputs an image signal of the observation object. The signal processing unit alternately repeats obtainment of a partial image signal using a part of a light receiving area of the imaging element and obtainment of a partial image signal using the remaining part of the light receiving area. The signal processing unit also obtains a whole image signal corresponding to an image of the observation object using a partial image signal obtained in the n-th (n is a natural number) obtainment and a partial image signal obtained in the (n+1)th obtainment. Further, a partial component of the n-th partial image signal is extracted by an extraction unit, and the extracted partial component is added to the (n+1)th partial image signal.

6 Claims, 2 Drawing Sheets

ELECTRONIC ENDOSCOPE APPARATUS

BACKGROUND OF THE INVENTION

1. Field of the Invention

The present invention relates to an electronic endoscope apparatus which alternately repeats obtainment of a partial image signal using a part of a light receiving area of an imaging element and obtainment of a partial image signal using the remaining part of the light receiving area, and which obtains an image signal corresponding to an image of an observation object using a partial image signal obtained in the n-th obtainment and a partial image signal obtained in the (n+1)th obtainment.

2. Description of the Related Art

Conventionally, various kinds of electronic endoscope apparatus which obtain color image signals by taking photographs of an image of an observation object by scope units which have imaging elements, and which display color images based on obtained color image signals have been proposed.

As the electronic endoscope apparatus described above, an electronic endoscope apparatus which obtains an image signal, for example, using a color filter, such as a complementary color filter, according to a chrominance line-sequential method has been proposed (please refer to Japanese Unexamined Patent Publication No. 11 (1999)-136693).

In the electronic endoscope apparatus according to the chrominance line-sequential method, signal electric charges of two adjacent pixels with respect to the vertical direction are added and read out. When the signal electric charges are added, signal electric charges of a different pair of adjacent pixels are added in an odd field and in an even field. Then, a whole image signal which represents a whole image is obtained using a partial image signal which is read out from the odd field and a partial image signal which is read out from the even field.

However, when, for example, a stomach or the like in a body cavity is photographed using an electronic endoscope apparatus according to the chrominance line-sequential method as described above, if the direction of the leading edge of a scope unit of the electronic endoscope apparatus is quickly changed from the stomach wall to the center of the stomach, the luminance of an image signal obtained in the odd field and that of an image signal obtained in the even field may be completely different from each other. In that case, a striped pattern is formed in a displayed image, and a so-called flicker is generated.

SUMMARY OF THE INVENTION

In view of the foregoing circumstances, it is an object of the present invention to provide an electronic endoscope apparatus which can suppress generation of the flicker which is generated in the electronic endoscope apparatus as described above.

An electronic endoscope apparatus according to the present invention is an electronic endoscope apparatus comprising:

an imaging element which obtains an image of an observation object at a light receiving area of the imaging element by receiving light reflected by the observation object when the observation object is illuminated with light, and which outputs an image signal of the observation object; and a signal processing unit which alternately repeats obtainment of a partial image signal using a part of the light receiving area of the imaging element and obtainment of a partial image signal using the remaining part of the light receiving area, and which obtains a whole image signal corresponding to an image of the observation object using a partial image signal obtained in the n-th (n is a natural number) obtainment and a partial image signal obtained in the (n+1)th obtainment, wherein the image processing unit includes an extraction unit for extracting a partial component of the n-th partial image signal and an addition unit for adding the partial component of the n-th partial image signal, extracted by the extraction unit, to the (n+1)th partial image signal.

Further, in the electronic endoscope apparatus, the extraction unit may extract a blurred image signal as the partial component by performing blur processing on the n-th partial image signal, and the addition unit may add the blurred image signal to the (n+1)th partial image signal.

In the electronic endoscope apparatus according to the present invention, a partial component of the n-th partial image signal is extracted, and the partial component of the n-th partial image signal is added to the (n+1)th partial image signal. Therefore, when field readout is performed, if a whole image signal is produced using a partial image signal of an odd field and a partial image signal of an even field, to which a partial component of the partial image signal of the odd field is added, and if the whole image of an observation object is displayed based on the whole image signal, it is possible to prevent production of the striped pattern in the whole image, as described above.

In the electronic endoscope apparatus, if blur processing is adopted as a method for extracting the partial component from the n-th partial image signal, it is possible to extract the partial component by simple operation processing.

DESCRIPTION OF THE PREFERRED EMBODIMENTS

Figure 1:
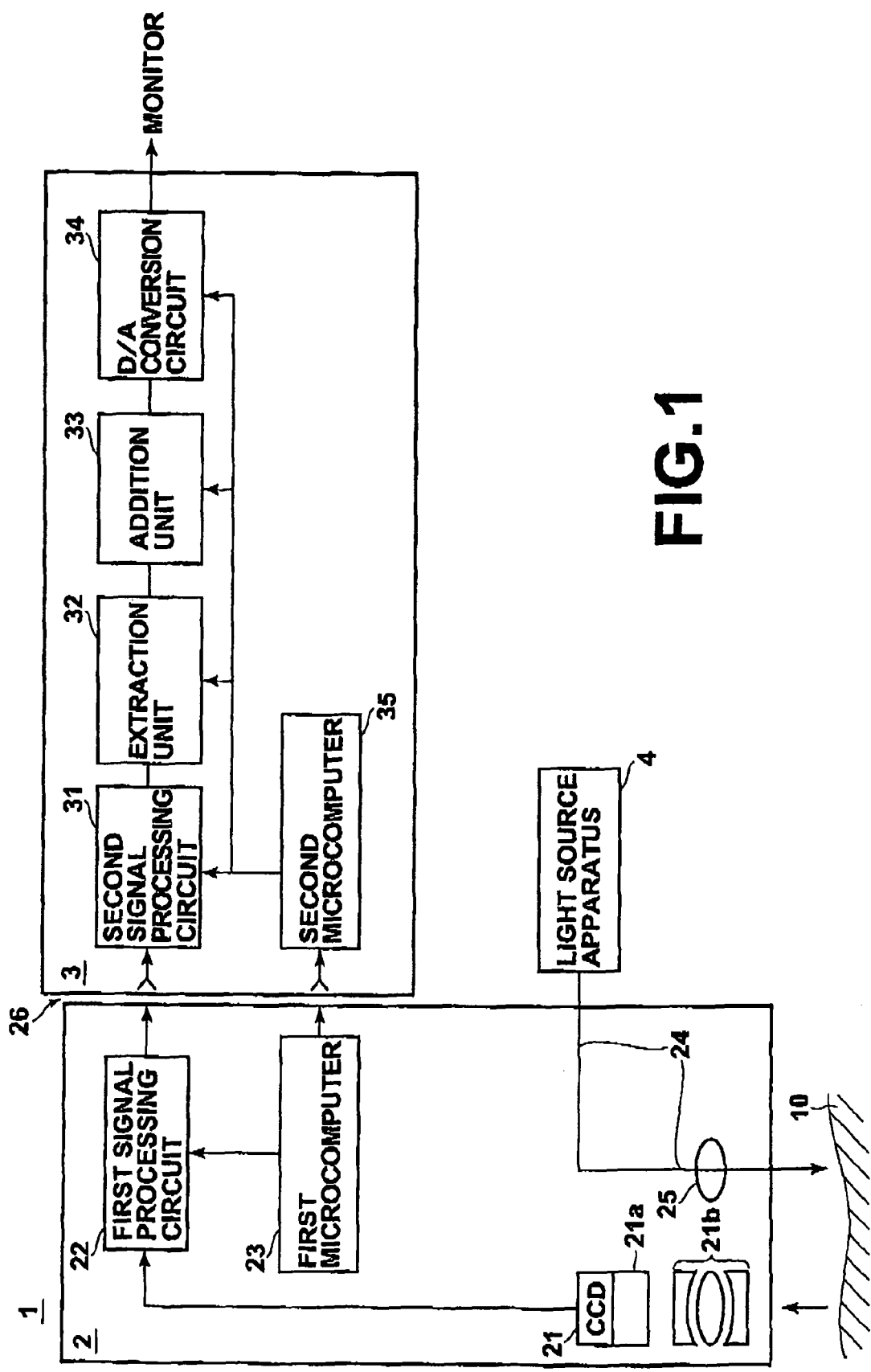
FIG. 1 is a block diagram illustrating the schematic configuration of an electronic endoscope apparatus according to an embodiment of the present invention.

Hereinafter, an embodiment of an electronic endoscope apparatus according to the present invention will be described with reference drawings. FIG. 1 is a block diagram illustrating the schematic configuration of the electronic endoscope apparatus according to the present invention.

As illustrated in FIG. 1, an electronic endoscope apparatus 1 according to the present invention includes a scope unit 2 which can be inserted into a body cavity or the like. The scope unit 2 obtains an image of an observation object 10 such as living tissue in the body cavity. The electronic endoscope apparatus 1 also includes a signal processing unit 3 which pet forms predetermined signal processing on a signal obtained by the scope unit 2, and produces a digital video signal for displaying an image on a monitor. The electronic endoscope apparatus 1 also includes a light source apparatus 4. The light source apparatus 4 outputs white light for illuminating the observation object 10 to the scope unit 2.

As illustrated in FIG. 1, the scope unit 2 includes a CCD 21 as an imaging element for obtaining an image of the observation object 10. The scope unit 2 also includes a first signal processing circuit 22 for performing predetermined processing on a signal obtained by the CCD 21. The scope unit 2 also includes a first microcomputer 23 which performs various kinds of control processing. The scope unit 2 also includes a lightguide means 24 which guides the illumination light output from the light source apparatus 4 to the leading edge of the scope unit 2. The scope unit 2 also includes an illumination lens 25 for illuminating the observation object 10 with the illumination light guided by the lightguide means 24. Further, an objective optical system 21b for forming an image of the observation object 10 on the CCD 21 is provided at the leading edge of the scope unit 2. The objective optical system 21b includes two concave lenses and a single convex lens, as illustrated in FIG. 1. Further, the scope unit 2 and the image processing unit 3 are connected to each other through a connector unit 26.

The CCD 21 is attached to the leading edge of the scope unit 2. The CCD 21 obtains an image of the observation object 10 by performing photoelectric conversion on light reflected at the observation object 10 when the observation object 10 is illuminated with illumination light. Further, a color filter 21a is provided on the CCD 21. The CCD 21 outputs a color image signal by performing photoelectric conversion on the light transmitted through the color filter 21a. The color filter 21a is a complementary color filter including four color components, namely a Cy (cyan) component, Mg (magenta) component, Ye (yellow) component and G (green) component. The color filter 21a is a filter which has a filter array according to a so-called chrominance line-sequential method. Further, in the CCD 21, signals are read out by using a so-called field readout method. In the field readout method, signals from an odd field and signals from an even field are separately read out. The color array of the color filter 21a and the field readout will be described later in detail.

The first signal processing circuit 22 performs signal processing such as correlated double sampling processing and automatic gain control and A/D conversion processing on the signal output from the CCD 21. The operation of the first signal processing circuit is controlled by the first microcomputer 23.

The signal processing unit 3 includes a second signal processing circuit 31. The second signal processing circuit 31 produces a digital video signal of an odd field and a digital video signal of an even field based on the signals output from the first signal processing circuit 22 of the scope unit 2. The signal processing unit 3 also includes an extraction unit 32. The extraction unit 32 extracts a partial component from the digital video signal of the odd field or even field, which is output from the second signal processing circuit 31. The signal processing unit 3 also includes an addition unit 33. The addition unit 33 adds the partial component extracted by the extraction unit 32 to a digital video signal of the odd field or a digital video signal of the even field. The signal processing unit 3 also includes a D/A (digital to analog) conversion circuit 34. The D/A conversion circuit 34 converts the digital video signal of the odd field and the digital video signal of the even field, which are output from the addition unit 33, into analog signals. The signal processing unit 3 also includes a second microcomputer 35. The second microcomputer 35 controls various kinds of signal processing as described above.

Next, an operation of the electronic endoscope apparatus according to the present embodiment will be described.

First, the leading edge of the scope unit 2 is inserted into the body cavity and led to the vicinity of the observation object in the body cavity. Then, the illumination light emitted from the light source apparatus 4 is guided by the lightguide means 24. The illumination light illuminates the observation object 10 through the illumination lens 25.

Then, when the observation object 10 is illuminated with the illumination light, the light is reflected by the observation object 10. Then, an image is formed on the imaging plane of the CCD 21 with the reflected light. The image is formed by the objective optical system 21b. At this time, the image is formed on the imaging plane of the CCD 21 with the light transmitted trough a color filter 21a provided on the CCD 21. Then, the CCD 21 performs photoelectric conversion on the image formed on the imaging plane of the CCD 21, and a signal produced by photoelectric conversion is read out by using the field readout method.

Figure 2:
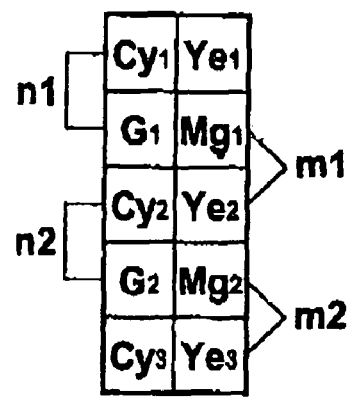
FIG. 2 is a diagram illustrating the color array of a color filter in the electronic endoscope apparatus illustrated in FIG. 1.

Here, the field readout will be described. The color array of the color filter 21a in the present embodiment is illustrated in FIG. 2. In FIG. 2, only a part of the color array of the color filter 21a is illustrated.

Then, signal electric charges of two adjacent pixels with respect to the vertical direction are added and read out. When the signal electric charges are added, signal electric charges of a different pair of adjacent pixels are added in an odd field and in an even field. Specifically, in the odd field, a signal of $(G_1+Cy_1)$ and a signal of $(Mg_1+Ye_1)$ are repeatedly read out from line n1, illustrated in FIG. 2. Then, a signal of $(G_2+Cy_2)$ and a signal of $(Mg_2+Ye_2)$ are repeatedly read out from line n2, illustrated in FIG. 2. Each line of the odd field is read out, and after the last line of the odd field is read out, readout of the even field starts. In the even field, a signal of $(G_1+Cy_2)$ and a signal of $(Mg_1+Ye_2)$ are repeatedly read out from line m1, illustrated in FIG. 2. Then, a signal of $(G_2+Cy_3)$ and a signal of $(Mg_2+Ye_3)$ are repeatedly read out from line m2, illustrated in FIG. 2. Each line of the even field is read out until the last line of the even field is read out.

Then, the signals which have been sequentially read out from the odd field and the even field, as described above, are input to the first signal processing circuit 22. In the first signal processing circuit, correlated double sampling processing, automatic gain control and A/D conversion processing, or the like is performed on the input signals. Then, digital image signals of the odd field and digital image signals of the even field are sequentially output from the first signal processing circuit 22. The digital image signals of the odd field and the digital image signals of the even field, which are output from the first signal processing circuit 22, are input to the second signal processing circuit 31 of the signal processing unit 3 through the connector unit 26.

Then, in the second signal processing circuit 31, a signal of (2R+3G+2B) which forms a luminance signal and a signal of (2B−G) and a signal of (2R−G), which correspond to chrominance signals, are calculated for each line of the odd field. The signals are calculated based on the digital image signal for each line of the odd field. After these signals are calculated, a signal of (2R+3G+2B) which forms a luminance signal and a signal of (2B−G) and a signal of (2R−G), which correspond to chrominance signals, are calculated for each line of the even field. The signals are calculated based on the digital image signal for each line of the even field in a manner similar to calculation of the signals in the odd field, as described above. The luminance signal and the chrominance signals may be obtained by using a well-known general obtainment method.

Then, the luminance signal and the chrominance signals of the odd field and those of the even field, which have been obtained as described above, are used, and the whole image is displayed. For example, when an image of a stomach or the like is photographed, the direction of the leading edge of the scope unit 2 may be quickly changed from the stomach wall to the center of the stomach in some cases. When the leading edge is quickly moved as described above, the value of the luminance signal obtained in the odd field and that of the luminance signal obtained in the even field may be completely different from each other. In that case, a striped pattern may be formed in a displayed whole image.

In the present embodiment, processing is performed as described below.

Figure 3A:
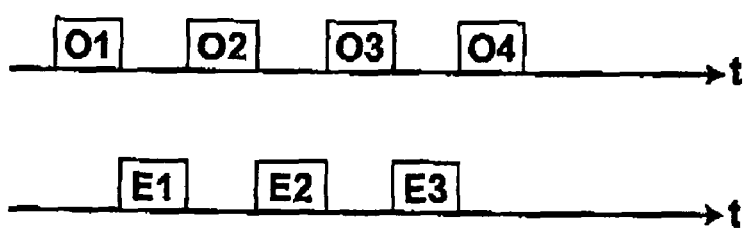
FIG. 3A is a diagram for explaining the operation of the electronic endoscope apparatus illustrated in FIG. 1.
Figure 3B:
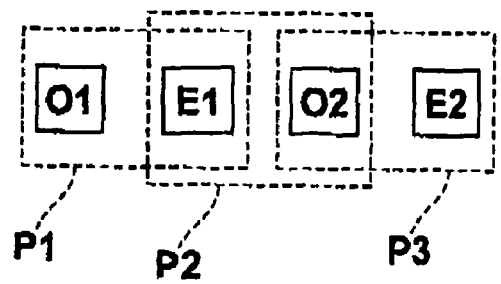
FIG. 3B is a diagram for explaining the operation of the electronic endoscope apparatus illustrated in FIG. 1

A luminance signal and chrominance signals of the odd field On (n is a natural number), which are calculated in the second signal processing circuit 31, and a luminance signal and chrominance signals of the even field En (n is a natural number), which are calculated in the second signal processing circuit 31, are output at the timing as illustrated in FIG. 3A. The output signals are input to the extraction unit 32. For example, when a whole image P1 is displayed based on the luminance signal and the chrominance signals of the odd field O1 and the luminance signal and the chrominance signals of the even field E1, blur processing is performed on the luminance signal of the odd field O1, and a blurred luminance signal is produced. It is preferable that blur processing is performed so that the ratio of the luminance information of the luminance signal before processing, namely the value of a signal of line n, to the value of a signal of line m is 50% to 50%. Blur processing may be performed by applying a Gaussian filter. However, the blur processing method is not limited to the method using the Gaussian filter. Any other well-known processing method may be adopted.

Then, the luminance signal and the chrominance signals of the odd field O1, the luminance signal and the chrominance signals of the even field E1, and the blurred luminance signal, which has been calculated as described above, are output from the extraction unit 32 to the addition unit 33. Then, the addition unit 33 adds the blurred luminance signal to the luminance signal of the even field. Here, it is preferable that blur processing is also performed on the luminance signal of the even field, to which the blurred luminance signal is added, so that the luminance information of the luminance signal of the even field is 50% of that of a blurred signal produced by blur processing.

Then, the luminance signal and chrominance signals of the odd field O1 and the luminance signal of the even field E1, to which the blurred luminance signal has been added, and chrominance signals of the even field E1 are output from the addition unit 33 to the D/A conversion circuit 34. Then, the signals are converted into analog signals at the D/A conversion circuit 34. The analog signals are output to a monitor, and a whole image P1 is displayed on the monitor based on the analog signals.

Next, when a whole image P2 is displayed based on the luminance signal and chrominance signals of the even field E1 and the luminance signal and chrominance signals of the odd field O2, blur processing is performed on the luminance signal of the even field E1 by the extraction unit 32, and a blurred luminance signal is produced.

Then, the luminance signal and chrominance signals of the even field E1, the luminance signal and chrominance signals of the odd field O2, and the blurred luminance signal, which has been calculated as described above, are output from the extraction unit 32 to the addition unit 33. Then, the blurred luminance signal is added to the luminance signal of the odd field O2 by the addition unit 33.

Then, the luminance signal and chrominance signals of the even field E1, the luminance signal of the odd field O2, to which the blurred luminance signal has been added, and chrominance signals of the odd field O2 are output from the addition unit 33 to the D/A conversion circuit 34. The signals are converted into analog signals at the D/A conversion circuit 34. The analog signals are output to the monitor, and the whole image P2 is displayed on the monitor based on the analog signals.

Next, when a whole image P3 is displayed based on the luminance signal and chrominance signals of the odd field O2 and the luminance signal and chrominance signals of the even field E2, blur processing is performed on the luminance signal of the odd field O2 by the extraction unit 32, and a blurred luminance signal is produced.

Then, the luminance signal and chrominance signals of the odd field O2, the luminance signal and chrominance signals of the even field E2, and the blurred luminance signal, which has been calculated as described above, are output from the extraction unit 32 to the addition unit 33. Then, the blurred luminance signal is added to the luminance signal of the even field E2 by the addition unit 33.

Then, the luminance signal and chrominance signals of the odd field O2, the luminance signal of the even field E2, to which the blurred luminance signal has been added, and chrominance signals of the even field E2 are output from the addition unit 33 to the D/A conversion circuit 34. The signals are converted into analog signals at the D/A conversion circuit 34. The analog signals are output to the monitor, and the whole image P3 is displayed on the monitor based on the analog signals.

Blur processing is sequentially performed on the luminance signal obtained in the previous field, as described above, and a blurred luminance signal is obtained. The blurred luminance signal is added to luminance signal of the next field. Then, a whole image is sequentially displayed based on the luminance signal of the field, to which the blurred luminance signal has been added, the chrominance signals of the field, and the luminance signal and chrominance signals of the previous field.

Since the whole image is displayed as described above, production of the striped pattern as described above can be prevented.

In the present embodiment, the luminance signal of the previous field, on which blur processing has been performed, is added to the luminance signal of the next field. Accordingly, the luminance information of the previous field contributes to the luminance information of the next field. Alternatively, as illustrated in table 1, the previous single line of a processing target line and the following single line of the processing target line may be extracted from the even field. Further, the previous single line of the processing target line and the following single line of the processing target line may be also extracted from the odd field. Then, the signal of the processing target line may be calculated by adding 30% of the signal of the processing target line, 20% of the signal of the previous line in the odd field, 20% of the signal of the following line in the odd field, 15% of the signal of the previous line in the even field, and 15% of the signal of the following line in the even field. Accordingly, the signals of the previous lines of the processing target line and those of the following lines of the processing target line contribute to the luminance information of the signal of the processing target line.

TABLE 1

| | |
|---|---|
| Even Field | 15% |
| Odd Field | 20% |
| Even Field Processing Target Line | 30% |
| Odd Field | 20% |
| Even Field | 15% |

Alternatively, the addition ratio of the signal of the previous field to the signal of the next field may be changed based on the difference in a brightness level therebetween. For example, if the difference in the brightness level between the previous field and the next field is 100% (for example, the color of the previous field is white and that of the next field is black, or vice versa), the value of the signal of the previous field and the value of the signal of the next field may be added at the ratio of 50% to 50%. Further, if the difference in the brightness level between the previous field and the next field is 50%, the value of the signal of the previous field and the value of the signal of the next field may be added at the ratio of 75% to 25% or 25% to 75%. Accordingly, the difference in the brightness becomes less noticeable.

Further, in the present embodiment, processing is performed so that the luminance information of the previous field contributes to that of the next field. However, it is also possible that processing is performed so that the color information of the previous field as well as the luminance information of the previous field contributes to the signal of the next field. Alternatively, it is also possible that processing is performed so that only the color information of the previous field contributes to the signal of the next field.

Further, in the embodiment as described above, descriptions were made on an electronic endoscope apparatus which performs field readout using a color filter according to the chrominance line-sequential method. However, the electronic endoscope apparatus according to the present invention may be also utilized as other kinds of electronic endoscope apparatus which perform interlace readout. In that case, a partial component of a partial image signal of the n-th field should be also extracted, and the partial component of the partial image signal of the n-th field should be added to the partial image signal of the (n+1)th field.

What is claimed is:

1. An electronic endoscope apparatus comprising:
   an imaging element which obtains an image of an observation object at a light receiving area of the imaging element by receiving light reflected by the observation object when the observation object is illuminated with light, and which outputs an image signal of the observation object; and
   a signal processing unit which alternately repeats obtainment of a first partial image signal using a part of the light receiving area of the imaging element and obtainment of a second partial image signal using a remaining part of the light receiving area, and which obtains a whole image signal corresponding to an image of the observation object using the first partial image signal obtained in an n-th (n is a natural number) obtainment and the second partial image signal obtained in an (n+1)th obtainment, wherein the image signal processing unit includes an extraction unit for extracting a blurred image signal, which is obtained by administering a blur process on at least one of a brightness component and a color component of the n-th partial image signal and an addition unit for adding the blur signal, extracted by the extraction unit, to the (n+1)th partial image signal.

2. An electronic endoscope apparatus as defined in claim 1, wherein the imaging element is provided with a color filter.

3. An electronic endoscope apparatus as defined in claim 2, wherein the color filter is a complementary color filter.

4. The apparatus of claim 1 wherein the first partial image signal is obtained from odd fields of the image signal from the imaging element, and wherein the second partial image is obtained from even fields of the image signal from the imaging element, and the whole image comprises a composite of the even fields and odd fields.

5. The apparatus of claim 4, wherein each of the odd fields and each of the even fields includes multiple color components, and blur processing is performed on the luminance.

6. The apparatus of claim 5, wherein the blur processing is performed on both the luminance and color components.

* * * * *